US010954928B2

(12) United States Patent
Bürli et al.

(10) Patent No.: US 10,954,928 B2
(45) Date of Patent: Mar. 23, 2021

(54) MICROPUMP

(71) Applicant: SENSILE MEDICAL AG, Olten (CH)

(72) Inventors: Fabian Bürli, Olten (CH); Alexandre Perrier, Liestal (CH); Thomas Wyss, Zuchwil (CH)

(73) Assignee: SENSILE MEDICAL AG, Olten (CH)

( * ) Notice: Subject to any disclaimer, the term of this patent is extended or adjusted under 35 U.S.C. 154(b) by 0 days.

(21) Appl. No.: 16/954,545

(22) PCT Filed: Dec. 10, 2018

(86) PCT No.: PCT/EP2018/084247
§ 371 (c)(1),
(2) Date: Jun. 17, 2020

(87) PCT Pub. No.: WO2019/121123
PCT Pub. Date: Jun. 27, 2019

(65) Prior Publication Data
US 2020/0309104 A1    Oct. 1, 2020

(30) Foreign Application Priority Data

Dec. 20, 2017    (EP) .................................. 17209179

(51) Int. Cl.
*F04B 7/06*    (2006.01)
*A61M 5/142*    (2006.01)
(Continued)

(52) U.S. Cl.
CPC .......... *F04B 7/06* (2013.01); *A61M 5/14216* (2013.01); *A61M 5/14236* (2013.01);
(Continued)

(58) Field of Classification Search
CPC . F04B 7/04; F04B 7/06; F04B 19/006; A61M 5/14216; A61M 2005/1402;
(Continued)

(56) References Cited

U.S. PATENT DOCUMENTS 7,726,955 B2    6/2010  Ryser et al.
8,282,366 B2 *  10/2012 Hilber .................... F04B 51/00
                                                      417/420
(Continued)

FOREIGN PATENT DOCUMENTS

EP    1 803 934    7/2007
EP    1 677 859    2/2010
(Continued)

OTHER PUBLICATIONS

Written Opinion in International Application No. PCT/EP2018/084247, dated Feb. 28, 2019, pp. 1-7.

*Primary Examiner* — Nathan C Zollinger
(74) *Attorney, Agent, or Firm* — Saliwanchik, Lloyd & Eisenschenk

(57) ABSTRACT

A pump including:
a stator (4),
a rotor (6) slidably and rotatably mounted at least partially in the stator, the rotor comprising a first axial extension (24) having a first diameter (D1) and a second axial extension (26) having a second diameter (D2) greater than the first diameter,
a first valve (V1) formed by a first valve seal (18) mounted on the stator around the first axial extension, in conjunction with a first channel (42) in the rotor that is configured to allow liquid communication across the first valve seal when the first valve is in an open position,
a second valve (V2) formed by a second valve seal (20) mounted on the stator around the second axial extension, in conjunction with a second channel (44) in the rotor that is configured to allow liquid communication across the second valve seal when the second valve is in an open position, and (Continued)

a pump chamber (8) formed between the rotor and stator and between the first valve seal and second valve seal. The pump further comprises a priming actuator (30) mounted on a housing of the stator and movable from a locked operating position to a priming position, the priming actuator (30) configured to engage and axially displace the rotor from an operating position in which at least one of the first and second valves is closed, to a priming position in which both first and second valves are open.

15 Claims, 8 Drawing Sheets

(51) Int. Cl.
  *F04B 19/00* (2006.01)
  *A61M 5/14* (2006.01)
(52) U.S. Cl.
  CPC ... *F04B 19/006* (2013.01); *A61M 2005/1402* (2013.01); *A61M 2205/103* (2013.01)

(58) Field of Classification Search
  CPC ......... A61M 2205/103; B05B 11/3042; B05B 3/0418; B05B 3/0427; B05B 3/0445
  See application file for complete search history.

(56) References Cited

U.S. PATENT DOCUMENTS

| | | | |
|---|---|---|---|
| 9,222,470 B2 * | 12/2015 | Genoud | A61M 5/14216 |
| 9,302,285 B2 * | 4/2016 | Marbet | B05B 11/3091 |
| 2007/0071596 A1 * | 3/2007 | Ryser | F04B 19/006 |
| | | | 415/172.1 |
| 2009/0123309 A1 * | 5/2009 | Hilber | F04B 51/00 |
| | | | 417/417 |
| 2010/0305508 A1 | 12/2010 | Franks | |
| 2014/0231549 A1 * | 8/2014 | Thiemer | B05B 11/3042 |
| | | | 239/333 |

FOREIGN PATENT DOCUMENTS

| | | |
|---|---|---|
| EP | 2 921 189 | 9/2015 |
| WO | WO 2006/037171 | 4/2006 |

* cited by examiner

MICROPUMP

CROSS-REFERENCE TO RELATED APPLICATION

This application is the U.S. national stage application of International Patent Application No. PCT/EP2018/084247, filed Dec. 10, 2018.

TECHNICAL FIELD

The present invention relates to a micropump. The micropump may be used for dispensing small quantities of liquid, in particular for use in medical applications, for instance in a drug delivery device. A micropump related to the invention may also be used in non-medical applications that require high precision delivery of small quantities of liquid.

DESCRIPTION OF RELATED ART

A micropump for delivering small quantities of liquid that may in particular be used in medical and non-medical applications is described in EP1803934 and in EP1677859. The micropump described in the aforementioned documents includes a rotor with first and second axial extensions of different diameters that engage with first and second seals of the stator to create first and second valves that open and close liquid communication across the respective seal as a function of the angular and axial displacement of the rotor. A pump chamber is formed between the first and second seals of the stator whereby the pumped volume of liquid per rotation cycle of the rotor is a function of both the difference in diameters between the first and second rotor axial extensions and the axial displacement of the rotor that is effected by a cam system as a function of the angular position of the rotor with respect to the stator. The ability to control the pumped volume per cycle as a function of the rotary and axial displacement of the rotor but also the difference in diameters between the rotary extensions enables to pump very small quantities of liquid per revolution of the rotor with high accuracy.

One of the advantageous features of the pumps described in the above-mentioned patents is the absence of a direct liquid communication between the inlet and outlet, because the inlet and outlet valves can never be open at the same time. This characteristic ensures safe operation of the pump in particular for medical applications whereby a drug may only be administered when the pump is being operated and liquid through-flow is automatically prevented when the pump stops operating at any position of the pump.

One of the drawbacks of this pump system however is that a priming operation of the pump can be slow and moreover friction between the pump shaft and valve seals upon initial operation occurs when the pump is empty and thus dry.

In certain applications, for example for infusion of a drug via a catheter tube, a large volume of liquid in comparison to the pump cycle volume of a pump as described in EP1803934 and in EP1677859 needs to be administered to prime and remove air in the infusion set. The priming procedure is thus not very efficient.

SUMMARY OF THE INVENTION

In view of the foregoing, an object of the invention is to provide a micropump that allows quick and reliable priming, yet that is precise and safe to operate.

It would be advantageous in particular to provide a micropump that allows quick priming in conjunction with a liquid delivery system downstream of the pump, such as an infusion set.

It would be advantageous to provide a pump that is easy to use and economical to manufacture.

In drug delivery applications, it is advantageous to provide a pump that can deliver very small quantities of liquid precisely, reliably and with high safety.

Objects of the invention are achieved by a micropump according to claim 1.

Disclosed herein is a pump including
a stator,
a rotor slidably and rotatably mounted at least partially in the stator, the rotor comprising a first axial extension having a first diameter and a second axial extension having a second diameter greater than the first diameter,
a first valve formed by a first valve seal mounted on the stator around the first axial extension, in conjunction with a first channel in the rotor that is configured to allow liquid communication across the first valve seal when the first valve is in an open position,
a second valve formed by a second valve seal mounted on the stator around the second axial extension, in conjunction with a second channel in the rotor that is configured to allow liquid communication across the second valve seal when the second valve is in an open position, and
a pump chamber formed between the rotor and stator and between the first valve seal and second valve seal.

According to the invention, the pump further comprises a priming actuator mounted on a housing of the stator and movable from a priming position to a locked operating position, the priming actuator configured to engage and axially displace the rotor from a priming position in which both first and second valves are open, to an operating position in which at least one of the first and second valves is closed.

The priming actuator may be positioned before initial use in the locked operating position and movable from the locked operating position to the priming position, the priming actuator configured to engage and axially displace the rotor from the operating position in which at least one of the first and second valves is closed, to the priming position in which both first and second valves are open. In this embodiment, the locking mechanism is releasable to allow the rotor to be moved from the operating position to the priming position.

In an alternative embodiment, the locking mechanism is irreversible to prevent the rotor from being moved from an operating position to a priming position, whereby prior to first use the rotor is in the priming position.

In an advantageous embodiment, the priming actuator is slidably mounted on a housing of the stator.

In an advantageous embodiment, the priming actuator comprises a locking mechanism comprises a locking shoulder engaging a complementary locking shoulder on the stator housing in the pump operating position.

In an advantageous embodiment, the locking mechanism comprises a pivotable latch.

In an advantageous embodiment, the pivotable latch comprises a manually engagable button connected via an integrally formed hinge to the priming actuator.

In an advantageous embodiment, the rotor comprises a rotor head formed at an end of the rotor shaft, the rotor head comprising an actuation rim extending therearound, the actuation rim comprising an inner axial shoulder engageable with an actuation shoulder of the priming actuator.

In an advantageous embodiment, the actuation rim comprises an outer axial shoulder configured to interfere with a rim axial control shoulder provided on the priming actuator when the priming actuator is in a locked operating position and the rotor is not in the operating position to prevent operation of the pump.

In an advantageous embodiment, the cam track is provided on an inner radial portion of the actuation rim and the inner axial shoulder engageable by the actuation shoulder is provided on an outer radial portion of the actuation rim.

In an advantageous embodiment, the rotor first extension comprises a recess proximate a free end of the first extension configured to increase the channel section for liquid through-flow to the inlet.

In an advantageous embodiment, the priming actuator comprises a head extending partially over a head of the rotor to block removal of the rotor from the stator.

In an advantageous embodiment, an inlet of the pump is connected to the pump chamber via the first valve and an outlet of the pump is connected to the pump chamber via the second valve, and wherein the inlet is positioned at an axial free end of a shaft of the rotor.

In an embodiment, the inlet may extend in a substantially radial direction from the rotor, and the outlet may extend in a substantially radial direction from the rotor.

In an advantageous embodiment, the stator is made of injected polymers, a first polymer for a body of the stator and a second polymer with elastic properties for the valve seals.

In an embodiment, the rotor is made of an injected polymer. In another embodiment, the rotor is made of metal, preferably steel.

Further objects and advantageous features of the invention will be apparent from the claims, from the detailed description, and annexed drawings, in which:

DETAILED DESCRIPTION OF EXEMPLARY EMBODIMENTS

Figure 1:
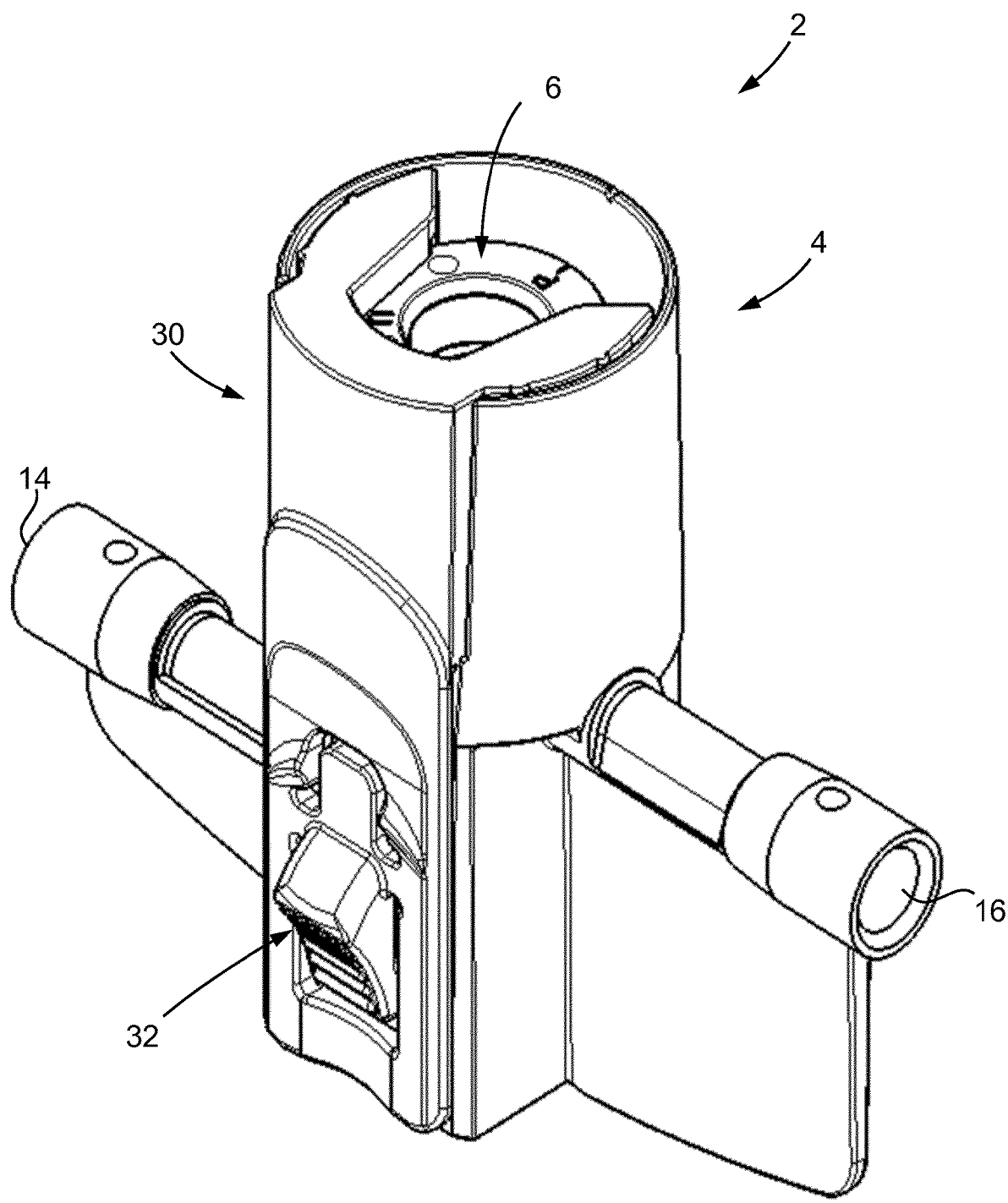
FIG. 1 is a perspective view of a pump module of a micropump according to an embodiment of the invention.
Figure 2:
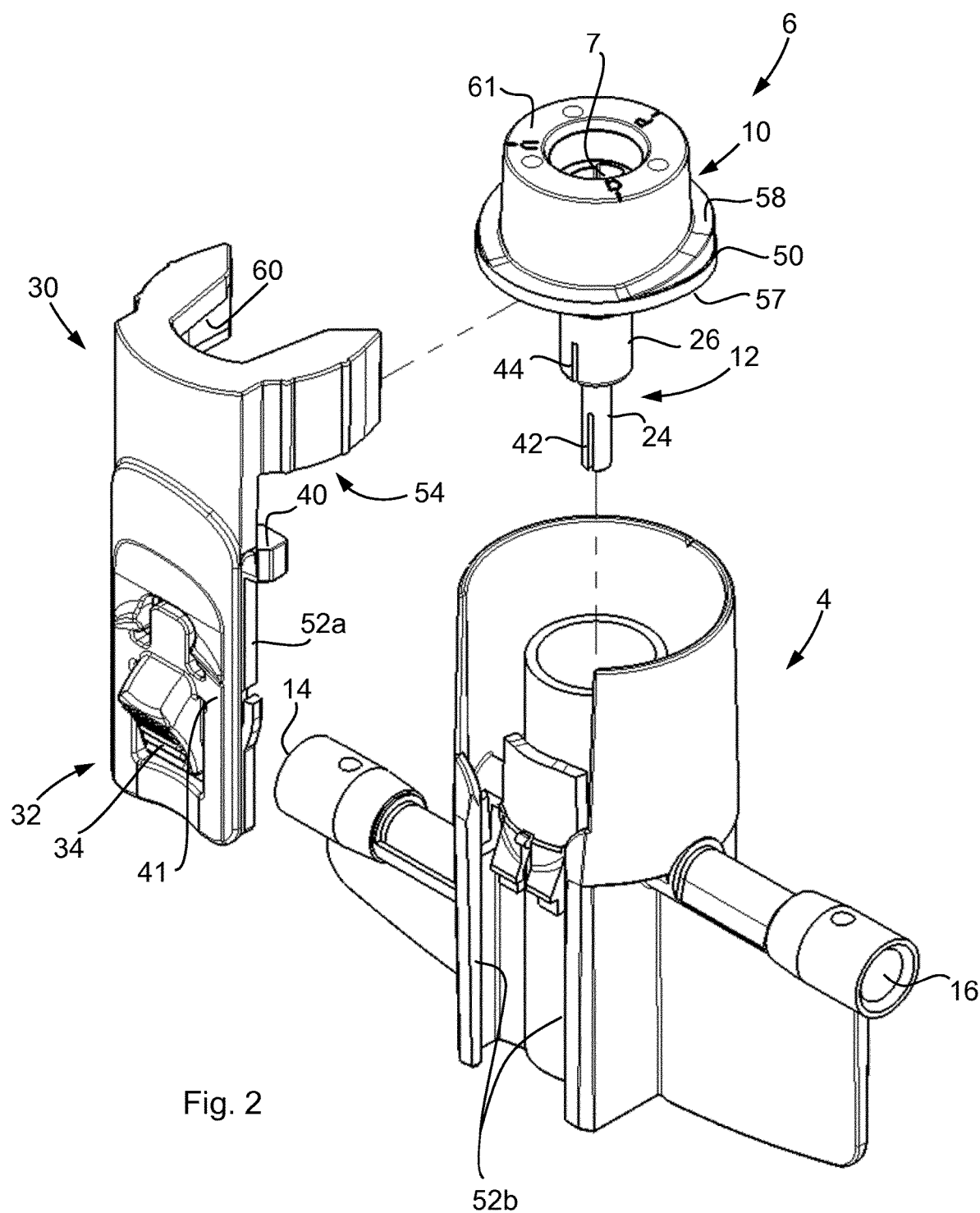
FIG. 2 is an exploded perspective view of the pump module of FIG. 1.

Referring to the figures, a micropump includes a pump module 2 comprising a stator 4 and a rotor 6 driven by a rotary drive (not shown) that imparts a rotational movement on the rotor about an axis of rotation A. The rotor 6 is biased axially, for instance by a spring (not shown), such that a camming system comprising a cam track on the rotor 46 engaging a complementary cam follower 48 on the stator imparts an axial displacement Ax of the rotor relative to the stator as a function of the angular position of the rotor as it turns. The axial and rotational displacement of the rotor relative to the stator causes first and second valves, which will be described in more detail hereinafter, to open and close in order to effect a pumping action. This general functioning principal is per se known and described for instance in EP1803934.

In an embodiment, the pump inlet 14 may be formed at an axial end of the rotor whereas an outlet 16 may be provided towards the end of the rotor comprising the cam. The outlet 16 may extend radially through the stator. The inlet and outlet may be inverted, depending on the rotational direction of the rotor relative to the stator and the valve seals configuration. Moreover, in certain embodiments, the pump may also be configured to be bidirectional whereby the direction of fluid flow depends on the direction of rotation of the rotor. The inlet or outlet formed at an axial end of the rotor may also be directed radially through the stator instead of axially from the end of the stator. The skilled person will appreciate that various fluid channels for the inlet and outlet may be configured according to the connection needs to fluid source and fluid delivery location without departing from the scope of the invention.

The rotor 6 has a first extension 24 having a first diameter D1, and a second extension 26 having a second diameter D2, the first and second diameters having different values. In the illustrated embodiment, the diameter D2 of the second extension 26 is larger diameter than the diameter D1 of the first extension 24. The difference in the first and second diameters coupled with the axial displacement of the rotor defines a pumped volume per revolution of the rotor.

The micropump comprises a first valve V1 formed between the rotor first extension and the stator and a second valve V2 formed between the rotor second extension and the stator. The first and second valves V1, V2, control the opening and closing of the corresponding inlet 14 or outlet 16.

The first valve V1 is formed by a first valve seal 18 mounted on the stator and a first channel 42 mounted on the rotor that is configured to allow liquid communication across the first valve seal when the first valve seal is in an open position, and to not allow liquid communication across the first valve seal when the first valve V1 is in a closed position. The second valve V2 is formed by a second valve seal 20 on the stator 4 and a second channel 44 formed on the rotor 6 that allows liquid communication across the second valve seal when the second valve V2 is in an open position, and to not allow liquid communication across the second valve seal when the second valve V2 is in a closed position. Between the rotor 6 and stator 4 and between the first valve seal 18 and second valve seal 20, a pump chamber 8 is formed. A pump chamber seal 22 circumscribes the second extension 26 and separates the pump chamber 8 from the pump external environment.

Within the scope of the invention, the first valve seal 18 and a second valve seal 20 may have various configurations and shapes provided that there is an oblique or axial offset in the seal that allows the first and second channels respectively to cross over the respective seals due to the angular and axial displacement of the rotor, to open and close the first and second valves as required during the filing and expulsion phases, without allowing liquid communication directly between the inlet and outlet.

In the illustrated embodiments, the liquid channels 42, 44 are illustrated as grooves extending axially in their respective first and second rotor extensions 24, 26. In a variant however, other liquid channel configurations may be implemented, for instance the channel may not be a groove but buried within the rotor and having orifices on the rotor surface that allow communication across the corresponding seal. It may further be noted that the first valve seal 18 may have a different angular orientation with respective the second valve seal 20 compared to the illustrated embodiment, and that the position of the rotor channel 44, 42 would be adapted accordingly.

The stator may be an injected component for instance an injected polymer with the seal being injected therein for instance in a two-step injection process. The seal may be injected in an elastomeric material as per se known in the art. The rotor 6 may also be injected polymer, the stator and rotor thus forming low cost disposable parts. The rotor 6 may however also be made of a more durable material such as steel or another metal. A metal rotor may be advantageous in certain applications to reduce wear or friction and/or increase dimensional accuracy of the rotor and thus of the pump cycle volume accuracy.

According to an aspect of the invention, the pump module 2 further comprises a priming actuator 30 movably mounted to a housing of the stator 4. The priming actuator 30 may be moved from a locked position as illustrated in FIGS. 1, 3a, 4a, 5a to a priming position shown in FIGS. 3b, 4b, 5b.

In the locked position, the pump module may be driven to administer a liquid by rotating the rotor as described hereinabove. During the operation of the pump, the first and second valves are never open at the same time and thus liquid may not pass freely from the inlet 14 to the outlet 16, or vice versa, when the rotor is not driven, irrespective of the rotational position of the rotor.

Before initial use of the pump, or after initial operation when the pump has been stopped, a priming operation may be carried out in order to fill the liquid channels through the pump and upstream and downstream of the pump. Channels include the inlet 14, pump chamber 8, and outlet 16, as well as fluid channels downstream or upstream of the pump. For instance, in a medical application where the pump is used for infusion of a drug via a catheter tube, the volume of liquid in the channels leading to the patient may be significantly larger than the volume of the pump chamber 8 and thus a priming operation relying only on the operation of the pump by rotation of the rotor 6 may be time-consuming.

According to the invention, the priming operation opens both valves V1, V2 to allow liquid to pass through the pump module 2 and the upstream and downstream liquid channels rapidly. The priming actuator 30 is configured to engage the rotor 6 to displace it axially in a direction that increases the volume of the pump chamber 8 until both inlet and outlet valves V1, V2 are open. The inlet valve V1 is open when the first channel 42 in the first rotor extension 24 crosses the first valve seal 18, and the outlet valve V2 is open when the second channel 44 in the second rotor extension 26 crosses the second valve seal 20.

In order to reduce resistance to fluid through-flow, the first extension 24 of the rotor may be advantageously provided with a cut away portion or recess 54 at a free end of the rotor shaft 12.

The priming actuator 30 comprises guide rails 52a engaging in complementary guide rails 52b on the stator housing allowing the priming actuator 30 to slide axially with respect to the stator housing. The priming actuator further comprises a releasable locking mechanism 32 which in the illustrated embodiment is in a form of a press-button latch 34 comprising a locking shoulder 36 that engages a locking shoulder 37 on the stator housing.

Figure 3A:
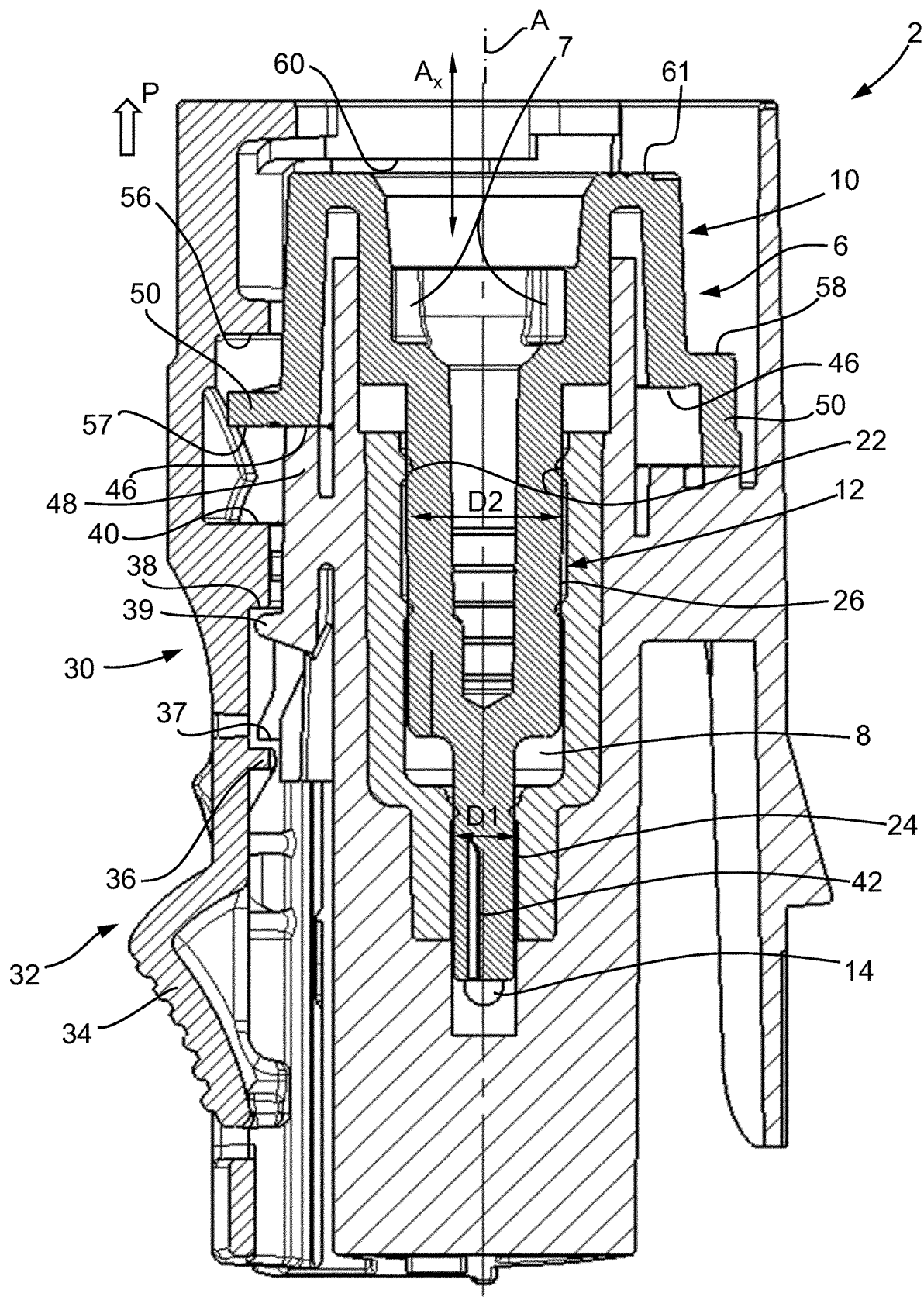
FIG. 3a is a cross-sectional view of the pump module of FIG. 1.
Figure 3B:
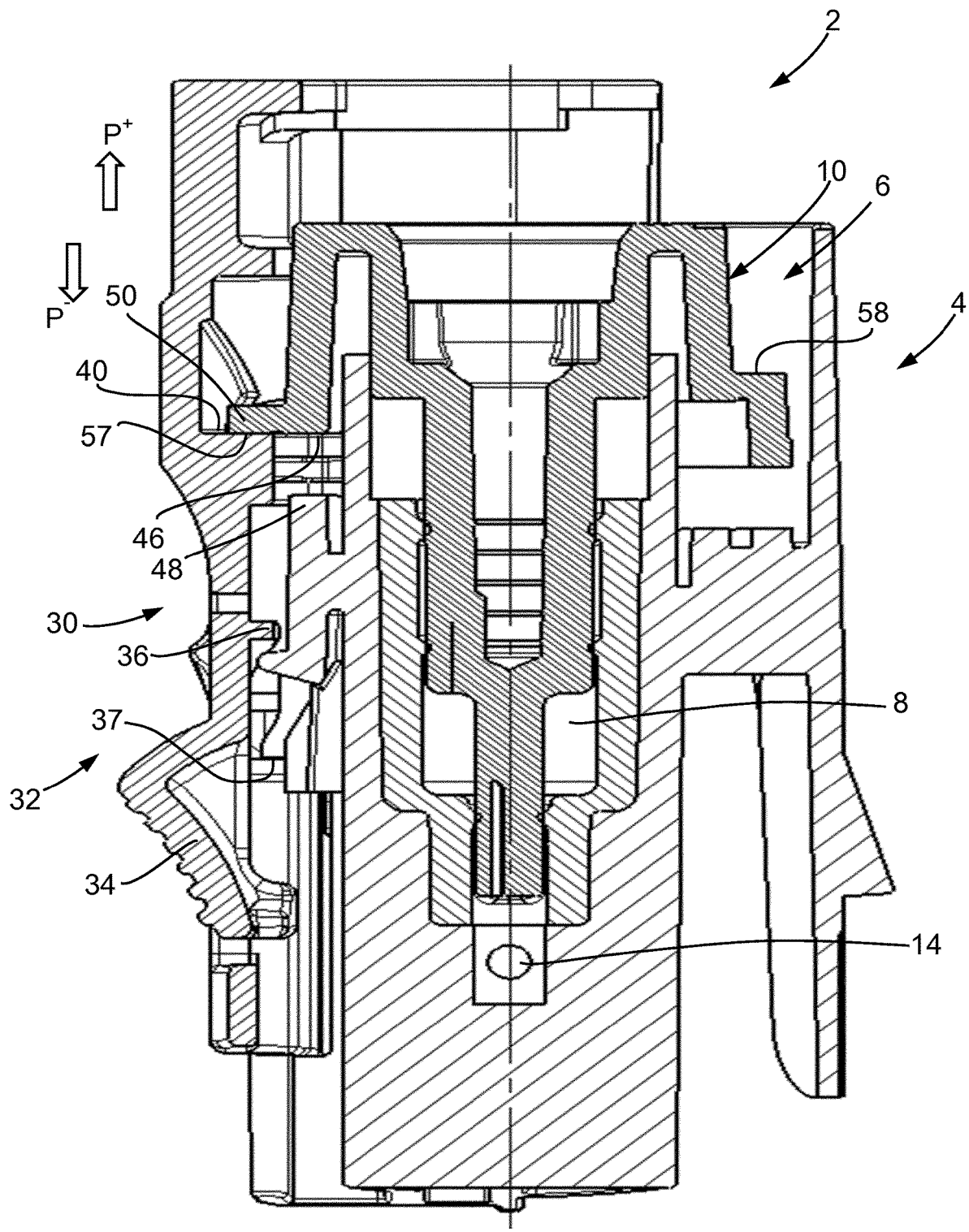
FIG. 3b is a view similar to FIG. 3a with a rotor of the pump module in a priming position.
Figure 4A:
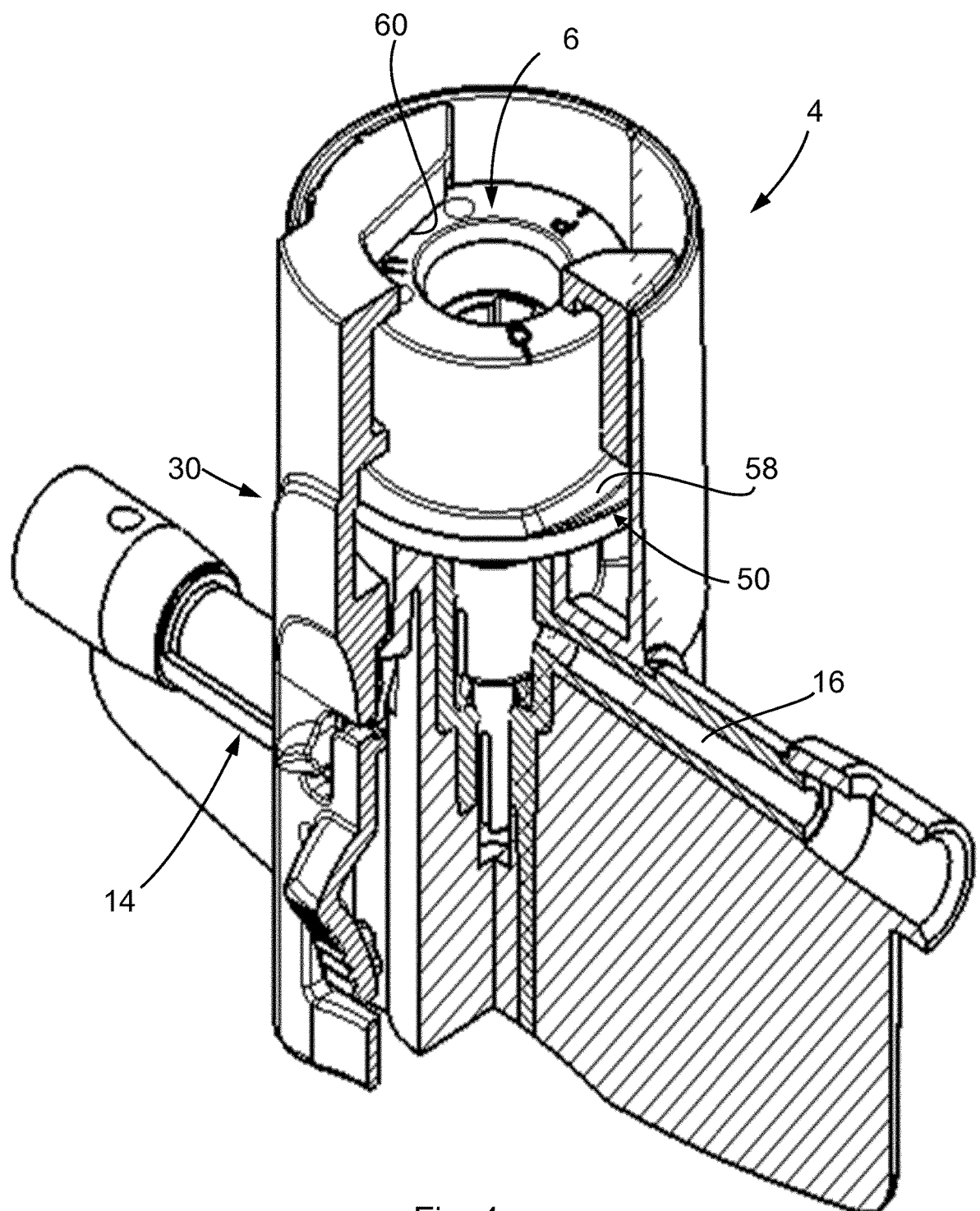
FIG. 4a is a perspective partial cross-sectional view of the micropump of FIG. 1.
Figure 4B:
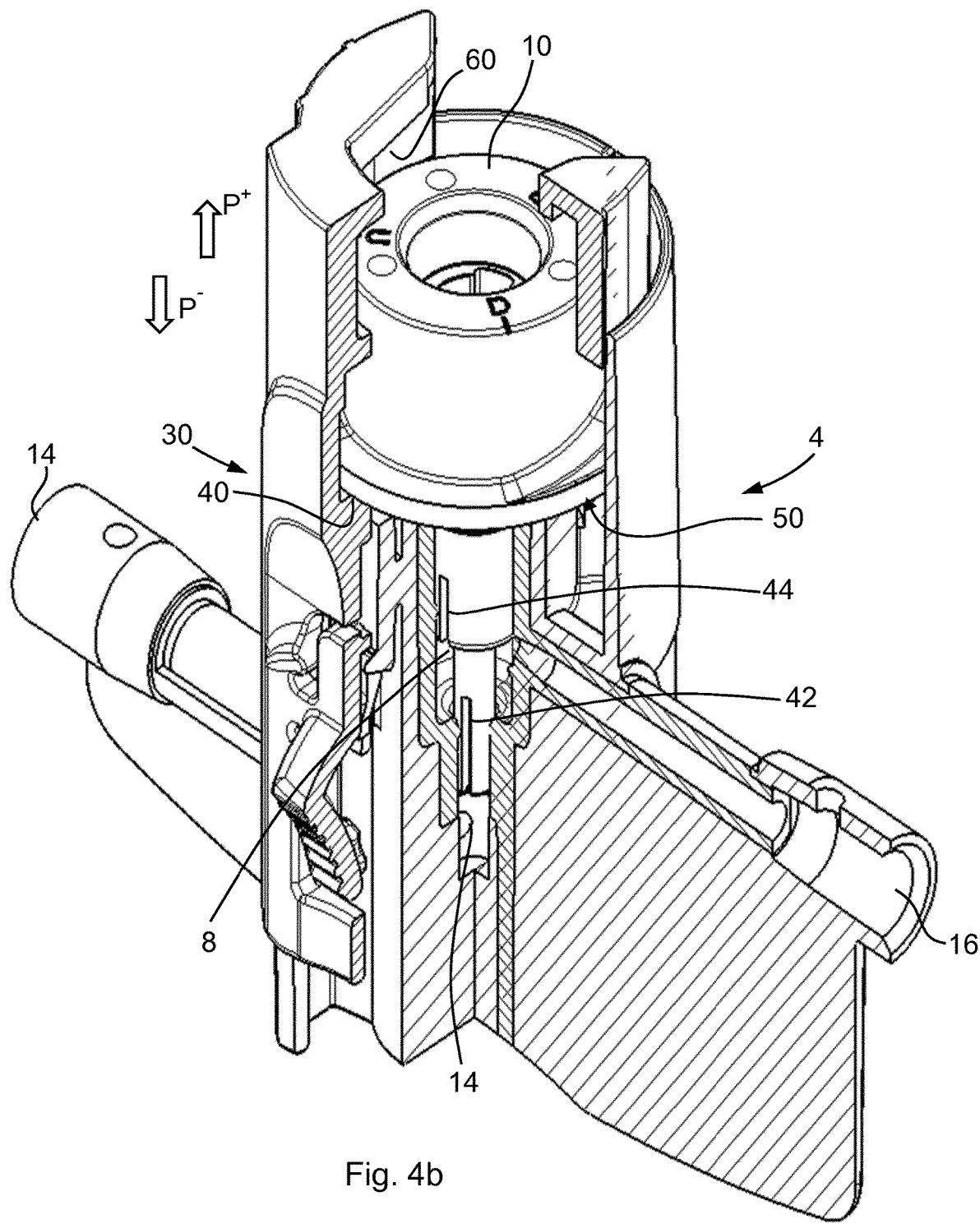
FIG. 4b is a view similar to FIG. 4a with a rotor of the pump module in a priming position.
Figure 5A:
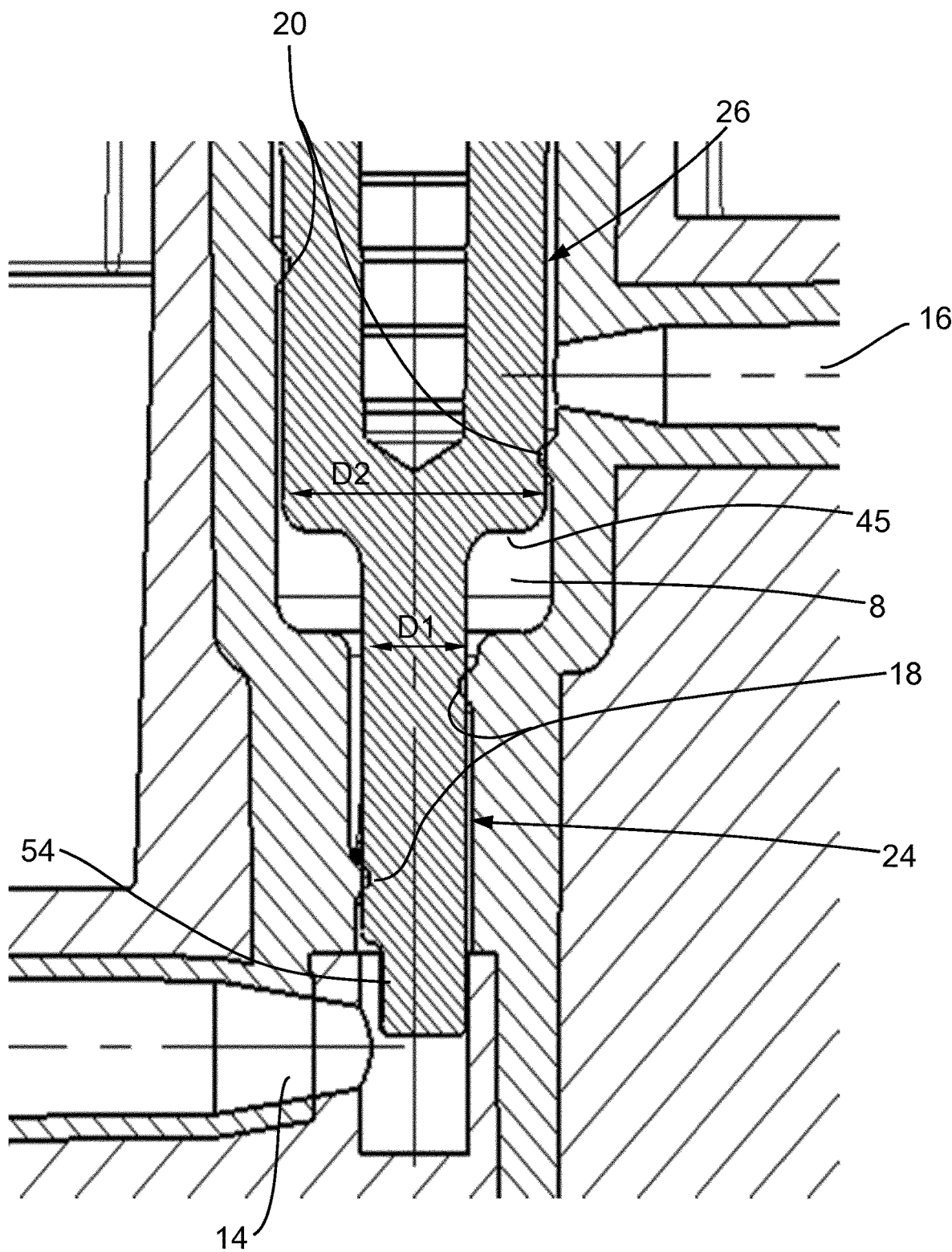
FIG. 5a is a detailed partial view of a pump chamber and rotor shaft portion of the pump module according to an embodiment of the invention.

During operation of the pump module as illustrated in FIGS. 3a, 4a and 5a, the priming actuator is in a locked position preventing the rotor 6 to be axially moved out of its operating position. For a priming operation, the locking mechanism 32 may be actuated to disengage the locking shoulder 36 thereof from the housing locking shoulder 37, followed by displacing the priming actuator 30 relative to the stator housing in a priming direction P+. The priming actuator is displaced until an actuation shoulder 40 on the priming actuator 30 engages a complementary shoulder 57 on the rotor head 10 and axially lifts the rotor away from the stator in the priming direction P+, which corresponds to a direction of increasing pump chamber volume, as illustrated in FIGS. 3b and 4b.

Figure 5B:
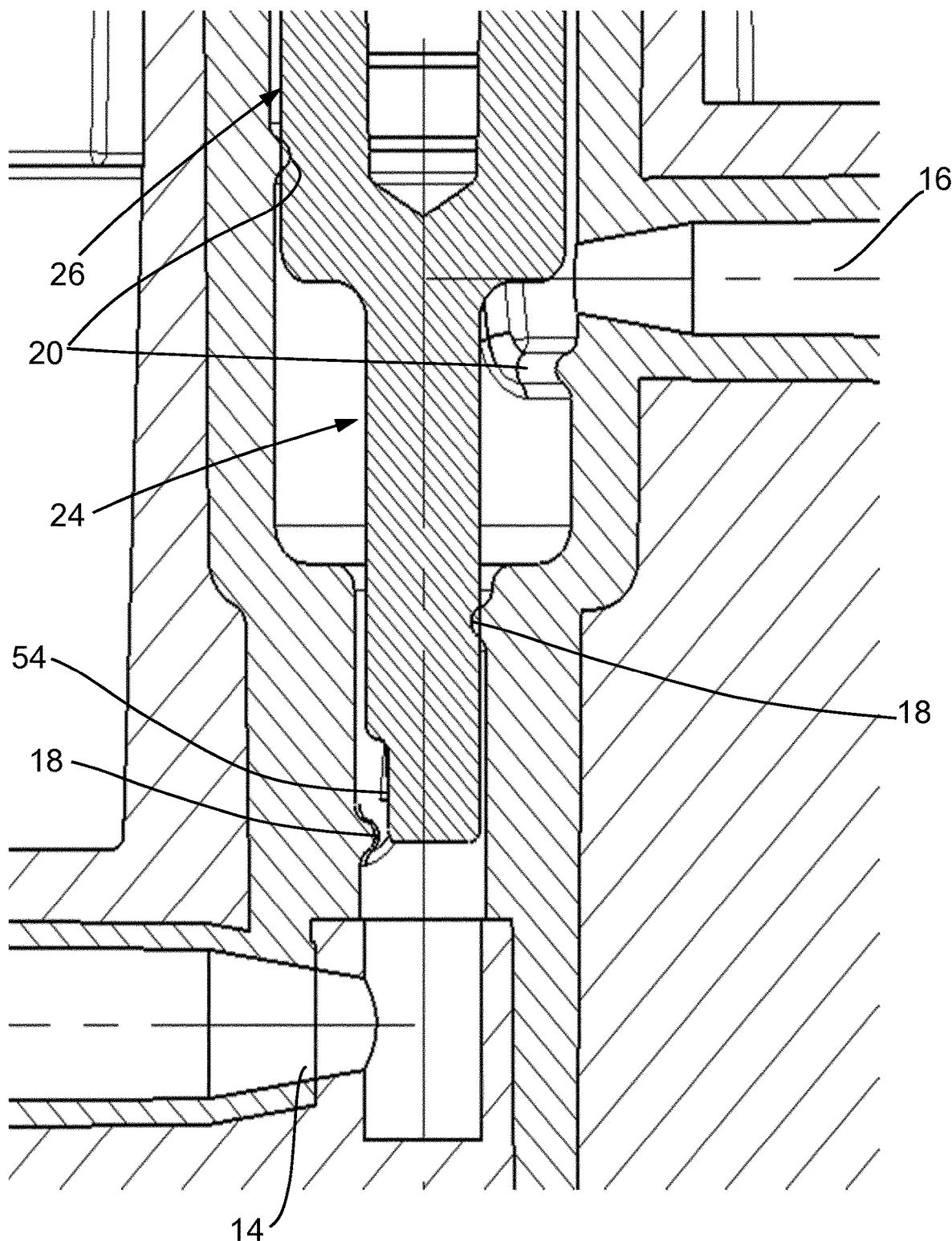
FIG. 5b is a view similar to FIG. 5a showing the rotor in a priming position.

In the illustrated embodiment, the rotor head 10 comprises an actuation rim 50 having an inner axial shoulder 57 configured to be engaged by the actuation shoulder 40 of the priming actuator 30. As best seen in FIG. 3b, the cam track 46 on the rotor is lifted certain distance away from the complementary cam follower 48 on the stator. As best seen in FIG. 5b, liquid can pass directly from the inlet 14 through the first channel 42 in the rotor first extension 24, into the pump chamber 8 and out through the outlet 16. Pressure applied by gravitational force or actively by a pressure generator on the liquid entering the inlet 14 can thus be used to rapidly deliver liquid through the pump during the priming operation.

Once the priming operation has been completed, the priming actuator 30 may be moved in the locking direction P-back to the locked position illustrated in FIG. 3a by a reverse axial sliding of the priming actuator 30 relative to the stator housing.

The stator housing may be provided with an actuator stop 39 configured to engage a complementary stop 38 provided on the priming actuator. The locking shoulder 36 of the locking mechanism 32 may also be configured to engage the actuator stop 39 on the stator such that the axial displacement of the priming actuator is limited and the priming actuator remains assembled to the stator housing and cannot be removed therefrom.

It may be noted that other stop and latch arrangements may be provided that allow locking of the priming actuator to the stator housing in the operating position, and unlocking and displacement thereof to the priming position, without departing from the scope of the invention. The skilled person understands that the stops may be provided in different positions on the actuator and stator housing, and that there are various locking mechanisms available for securing a first part mounted to a second part. In the illustrated embodiment, the priming actuator 30 is shown as slidably mounted to the stator housing and provided as separate part from the stator housing. However, in a variant, the priming actuator could be rotatably mounted on the stator housing in a manner such that rotation of the priming actuator relative to the stating housing causes an axial displacement of the priming actuator that in turn engages the rotor to lift it upon the operating position to the priming position.

In the illustrated embodiment, the priming actuator 30 comprises a head portion 54 that comprises an essentially U-shaped part partially surrounding the head 10 of the rotor and fitting in a cylindrical cavity of the stator housing. The head portion 54 comprises a rotor axial blocking shoulder 60 that extends over an edge 61 of the rotor head 10 thus ensuring that the rotor 6 may not be removed from the stator 4. The head portion 54 also provides a stable and secure anchoring of the priming actuator 30 to the stator housing.

The hinge 41 of the releasable locking mechanism 32 may be in a form of an integrally molded web connecting the button 35 of the locking mechanism to the rest of the priming actuator 30. In order to move the rotor 6 from the operating position to the priming position, the latch button 35 may be pressed by a user and simultaneously pushed in the priming direction P+ such that the priming actuator 30 is unlocked and axially displaced from the operating position to the priming position.

In the illustrated embodiment, the cam track 46 on the rotor head is provided on an inner radial position with regard to the outer periphery of the rim 50, the outer portion of the rim 50 serving for engagement with the actuation shoulder 40 of the priming actuator 30. As the cam track 46 defines a varying axial profile as a function of the angular position of the rotor, axial displacement of the rotor 6 relative to the stator 4 is imposed by the cam track 46 pressing on the cam follower 48.

An outer axial control shoulder 58 may be provided on the actuation rim 50, serving to ensure that the rotor 6 is in the correct axial operating position before the normal operation of the pump module. In this regard, the priming actuator 30 is provided with an axial control shoulder 56 that allows rotation of the rotor in its operating position, but that engages the outer axial shoulder 58 of the rotor head rim if it is in an incorrect axial position where the cam track 46 is not biased against the cam follower 48.

According to a variant (not shown) of the invention, the rotor may be supplied in a priming position prior to first use, and moved to a locked operating position after priming, or without priming, when the pump is put in a condition for use. In such a variant, the locking mechanism for the rotor may be reversible or irreversible. In a variant with an irreversible locking mechanism, after the rotor is moved from the priming position to the operating position, it can no longer be released from the operating position. Various irreversible locking latches and locking systems may be implemented to accomplish the one-way locking function.

List of features illustrated

Micropump
  Pump Module 2
    Stator 4
      Inlet 14
      Outlet 16
        Complementary locking mechanism 33
          Locking shoulder 37
          Actuator stop 39
        Complementary guide rails 52b
    Priming actuator 30
      Guide rails 52a
      Head 54
        Rotor axial blocking shoulder 60
        Rim axial control shoulder 56
        Locking mechanism 32
          Press-button Latch (pivotable) 34
            Locking shoulder 36
            Hinge 41
            Stop 38
          Actuation shoulder 40
    First valve V1
      First valve seal 18
    Second valve V2
      Second valve seal 20
      Pump chamber seal 22
    Rotor 6
    Coupling interface 7
    Rotor head 10
      Actuation Rim 50
        Outer axial shoulder 58

-continued

List of features illustrated

Inner axial shoulder 57
      Cam track 46
    Rotor shaft 12
      First extension (having a first diameter ) 24
        First channel 42
        Recess 54
      Second extension (having a second diameter) 26
        Second channel 44
        End 45 (connection to first extension)
      Pump chamber (formed between the rotor and stator) 8
      Axial displacement system
        Camming system
          Cam track on rotor 46
          Complementary cam follower on stator 48
Rotary Drive

The invention claimed is:

1. A pump including
a stator,
a rotor slidably and rotatably mounted at least partially in the stator, the rotor comprising a first axial extension having a first diameter and a second axial extension having a second diameter greater than the first diameter,
a first valve formed by a first valve seal mounted on the stator around the first axial extension, in conjunction with a first channel in the rotor that is configured to allow liquid communication across the first valve seal when the first valve is in an open position,
a second valve formed by a second valve seal mounted on the stator around the second axial extension, in conjunction with a second channel in the rotor that is configured to allow liquid communication across the second valve seal when the second valve is in an open position, and
a pump chamber formed between the rotor and stator and between the first valve seal and second valve seal, wherein
the pump further comprises a priming actuator mounted on a housing of the stator and movable from a priming position to a locked operating position, the priming actuator configured to engage and axially displace the rotor from a priming position in which both first and second valves are open, to an operating position in which at least one of the first and second valves is closed.

2. The pump according to claim 1, wherein the priming actuator comprises a locking mechanism comprising a locking shoulder engaging a complementary locking shoulder on the stator housing in the pump operating position.

3. The pump according to claim 1, wherein the priming actuator is slidably mounted on the housing of the stator.

4. The pump according to claim 1, wherein the rotor comprises a rotor head formed at an end of a shaft of the rotor, the rotor head comprising an actuation rim extending therearound, the actuation rim comprising an inner axial shoulder engageable with an actuation shoulder of the priming actuator.

5. The pump according to claim 1, wherein the rotor's first axial extension comprises a recess proximate a free end of the first extension configured to increase a channel section for liquid through-flow to an inlet.

6. The pump according to claim 1, wherein the priming actuator comprises a head extending partially over a head of the rotor to block removal of the rotor from the stator.

7. The pump according to claim 1, wherein an inlet of the pump is connected to the pump chamber via the first valve and an outlet of the pump is connected to the pump chamber via the second valve, and wherein the inlet is positioned at an axial free end of a shaft of the rotor.

8. The pump according to claim 7, wherein the inlet extends in a substantially radial direction from the rotor, and the outlet extends in a substantially radial direction from the rotor.

9. A pump including
a stator,
a rotor slidably and rotatably mounted at least partially in the stator, the rotor comprising a first axial extension having a first diameter and a second axial extension having a second diameter greater than the first diameter,
a first valve formed by a first valve seal mounted on the stator around the first axial extension, in conjunction with a first channel in the rotor that is configured to allow liquid communication across the first valve seal when the first valve is in an open position,
a second valve formed by a second valve seal mounted on the stator around the second axial extension, in conjunction with a second channel in the rotor that is configured to allow liquid communication across the second valve seal when the second valve is in an open position, and
a pump chamber formed between the rotor and stator and between the first valve seal and second valve seal, wherein
the pump further comprises a priming actuator mounted on a housing of the stator and movable from a priming position to a locked operating position, the priming actuator configured to engage and axially displace the rotor from a priming position in which both first and second valves are open, to an operating position in which at least one of the first and second valves is closed,
wherein the priming actuator comprises a locking mechanism comprising a locking shoulder engaging a complementary locking shoulder on the stator housing in the pump operating position,
wherein the locking mechanism is releasable to allow the rotor to be moved from an operating position to a priming position, the priming actuator configured to engage and axially displace the rotor from the operating position to the priming position.

10. The pump according to claim 9, wherein prior to first use the priming actuator is positioned in the locked operating position.

11. A pump including
a stator,
a rotor slidably and rotatably mounted at least partially in the stator, the rotor comprising a first axial extension having a first diameter and a second axial extension having a second diameter greater than the first diameter,
a first valve formed by a first valve seal mounted on the stator around the first axial extension, in conjunction with a first channel in the rotor that is configured to allow liquid communication across the first valve seal when the first valve is in an open position,
a second valve formed by a second valve seal mounted on the stator around the second axial extension, in conjunction with a second channel in the rotor that is configured to allow liquid communication across the second valve seal when the second valve is in an open position, and
a pump chamber formed between the rotor and stator and between the first valve seal and second valve seal, wherein
the pump further comprises a priming actuator mounted on a housing of the stator and movable from a priming position to a locked operating position, the priming actuator configured to engage and axially displace the rotor from a priming position in which both first and second valves are open, to an operating position in which at least one of the first and second valves is closed,
wherein the priming actuator comprises a locking mechanism comprising a locking shoulder engaging a complementary locking shoulder on the stator housing in the pump operating position,
wherein the locking mechanism comprises a pivotable latch.

12. The pump according to claim 11, wherein the pivotable latch comprises a manually engagable button connected via an integrally formed hinge to the priming actuator.

13. A pump including
a stator,
a rotor slidably and rotatably mounted at least partially in the stator, the rotor comprising a first axial extension having a first diameter and a second axial extension having a second diameter greater than the first diameter,
a first valve formed by a first valve seal mounted on the stator around the first axial extension, in conjunction with a first channel in the rotor that is configured to allow liquid communication across the first valve seal when the first valve is in an open position,
a second valve formed by a second valve seal mounted on the stator around the second axial extension, in conjunction with a second channel in the rotor that is configured to allow liquid communication across the second valve seal when the second valve is in an open position, and
a pump chamber formed between the rotor and stator and between the first valve seal and second valve seal, wherein
the pump further comprises a priming actuator mounted on a housing of the stator and movable from a priming position to a locked operating position, the priming actuator configured to engage and axially displace the rotor from a priming position in which both first and second valves are open, to an operating position in which at least one of the first and second valves is closed,
wherein the priming actuator comprises a locking mechanism comprising a locking shoulder engaging a complementary locking shoulder on the stator housing in the pump operating position,
wherein the locking mechanism is irreversible to prevent the rotor from being moved from an operating position to a priming position, whereby prior to first use the rotor is in a priming position.

14. A pump including
a stator,
a rotor slidably and rotatably mounted at least partially in the stator, the rotor comprising a first axial extension having a first diameter and a second axial extension having a second diameter greater than the first diameter, a first valve formed by a first valve seal mounted on the stator around the first axial extension, in conjunction with a first channel in the rotor that is configured to allow liquid communication across the first valve seal when the first valve is in an open position, a second valve formed by a second valve seal mounted on the stator around the second axial extension, in conjunction with a second channel in the rotor that is configured to allow liquid communication across the second valve seal when the second valve is in an open position, and a pump chamber formed between the rotor and stator and between the first valve seal and second valve seal, wherein the pump further comprises a priming actuator mounted on a housing of the stator and movable from a priming position to a locked operating position, the priming actuator configured to engage and axially displace the rotor from a priming position in which both first and second valves are open, to an operating position in which at least one of the first and second valves is closed, wherein the rotor comprises a rotor head formed at an end of a shaft of the rotor, the rotor head comprising an actuation rim extending therearound, the actuation rim comprising an inner axial shoulder engageable with an actuation shoulder of the priming actuator, wherein the actuation rim comprises an outer axial shoulder configured to interfere with a rim axial control shoulder provided on the priming actuator when the priming actuator is in a locked operating position and the rotor is not in the operating position to prevent operation of the pump.

15. A pump including a stator, a rotor slidably and rotatably mounted at least partially in the stator, the rotor comprising a first axial extension having a first diameter and a second axial extension having a second diameter greater than the first diameter, a first valve formed by a first valve seal mounted on the stator around the first axial extension, in conjunction with a first channel in the rotor that is configured to allow liquid communication across the first valve seal when the first valve is in an open position, a second valve formed by a second valve seal mounted on the stator around the second axial extension, in conjunction with a second channel in the rotor that is configured to allow liquid communication across the second valve seal when the second valve is in an open position, and a pump chamber formed between the rotor and stator and between the first valve seal and second valve seal, wherein the pump further comprises a priming actuator mounted on a housing of the stator and movable from a priming position to a locked operating position, the priming actuator configured to engage and axially displace the rotor from a priming position in which both first and second valves are open, to an operating position in which at least one of the first and second valves is closed, wherein the rotor comprises a rotor head formed at an end of a shaft of the rotor, the rotor head comprising an actuation rim extending therearound, the actuation rim comprising an inner axial shoulder engageable with an actuation shoulder of the priming actuator, wherein a cam track is provided on an inner radial portion of the actuation rim and the inner axial shoulder engageable by the actuation shoulder is provided on an outer radial portion of the actuation rim.

* * * * *